US00PP14308P39

(12) United States Plant Patent
Hachmann

(10) Patent No.: US PP14,308 P3
(45) Date of Patent: Nov. 18, 2003

(54) HOLLY PLANT NAMED 'HECKENSTAR'

(50) Latin Name: *Ilex meservae×aquitolium*
Varietal Denomination: Heckenstar

(75) Inventor: Hans Hachmann, Barmstedt (DE)

(73) Assignee: H. Hachmann Baumschulen GbR (DE)

( * ) Notice: Subject to any disclaimer, the term of this patent is extended or adjusted under 35 U.S.C. 154(b) by 0 days.

(21) Appl. No.: 10/127,243

(22) Filed: Apr. 22, 2002

(65) Prior Publication Data

US 2003/0200588 P1 Oct. 23, 2003

(51) Int. Cl.[7] ..... A01H 5/00

(52) U.S. Cl. ..... Plt./247

(58) Field of Search ..... Plt./247, 248

*Primary Examiner*—Bruce R. Campell
*Assistant Examiner*—Susan B. McCormick
(74) *Attorney, Agent, or Firm*—Webb Ziesenheim Logsdon Orkin & Hanson P.C.

(57) ABSTRACT

A male holly plant named 'Heckenstar' having an upright growth habit, glossy leaves, and tolerance to temperatures to −25° C.

6 Drawing Sheets

Classification: *Ilex meservae×aquitolium.*
Varietal denomination: 'Heckenstar'.

BACKGROUND OF THE INVENTION

The present invention comprises a new and distinct cultivar of *Ilex meservae×aquitolium* (holly) known by the varietal name 'Heckenstar'. The new variety was discovered in 1998 in a selected breeding program in Barmstedt, Germany and is a selection from the cross of the unpatented variety of *Ilex aquitolium* 'Pyramidalis' and the *Ilex meservae* variety 'Blue Prince' (U.S. Plant Pat. No. 3,517).

The plant was first asexually reproduced by cuttings in Barmstedt, Germany in October 1997 and has been asexually reproduced by cuttings in Barmstedt, Germany. The distinguishing features of this new cultivar are stable and reproduce true to type in successive propagations.

The following traits are determined to be basic characteristics of this new cultivar which in combination distinguish this variety as new and distinct:

1. Strict upright habit, pyramidal, bushy.
2. Well branched as young plant.
3. Excellent hardiness, up to −25° C.
4. Typical bluish, violet bark.
5. Glossy leaves, serrated not pricking.
6. Strong grower, at least 50 up to 80 cm per year for the male variety.

The following characteristics distinguish over the new variety from 'Blue Prince' and the unpatented variety 'Bare Stallion'.

1. More well-rounded habit and well branched as a young plant.
2. Habit more pyramidal, close upright.
3. Less trimming required.
4. Forms a close hedge more quickly.

DESCRIPTION OF THE DRAWINGS

The accompanying photographic drawings illustrate the new cultivar, the color being as nearly true as possible with color illustrations of this type. The photographs were taken under natural light conditions in Barmstedt, Germany.

DESCRIPTION OF THE NEW PLANT

Figure 1:
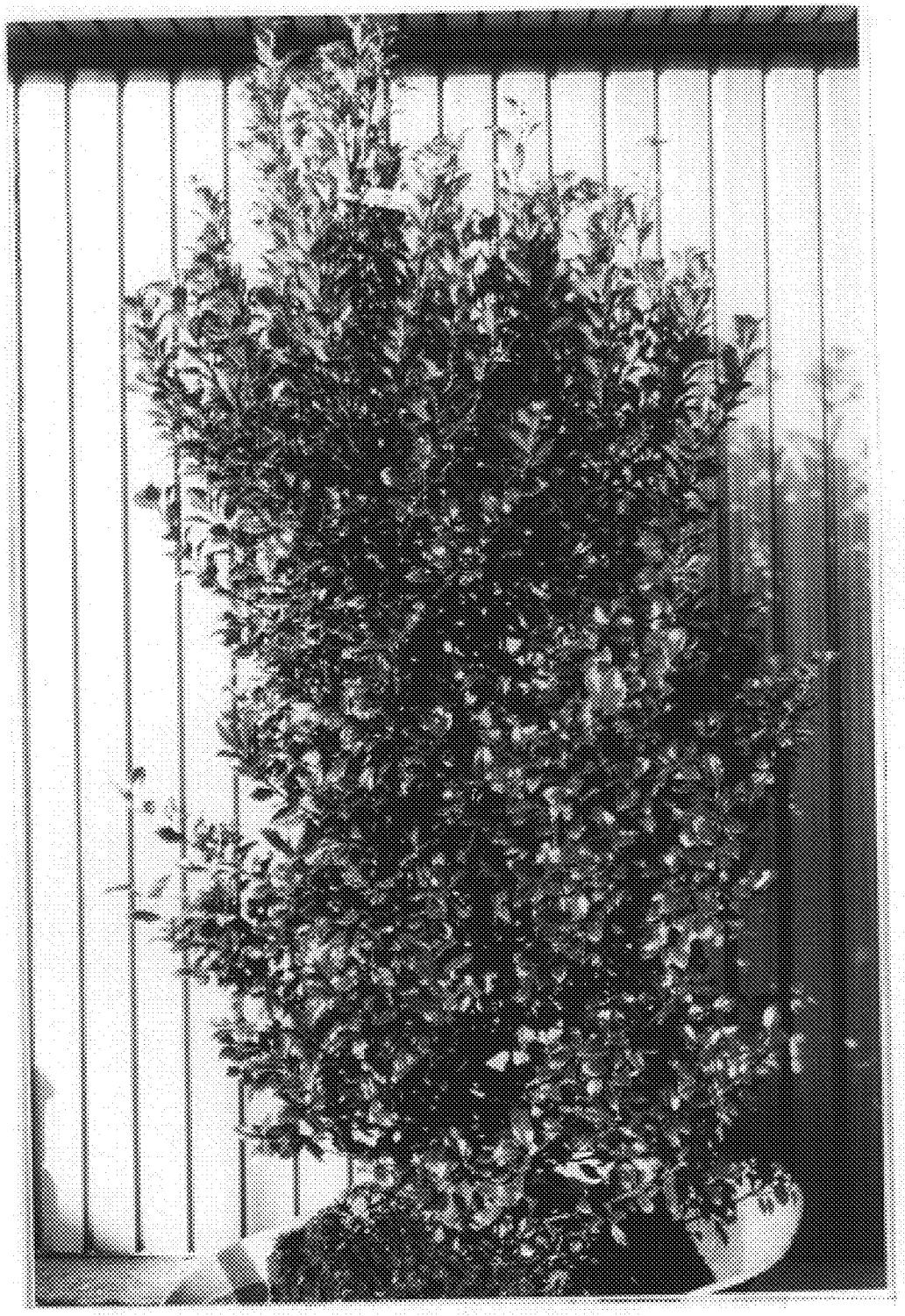
FIG. 1 shows the tree, 8 years old, about 180 cm tall.
Figure 2:
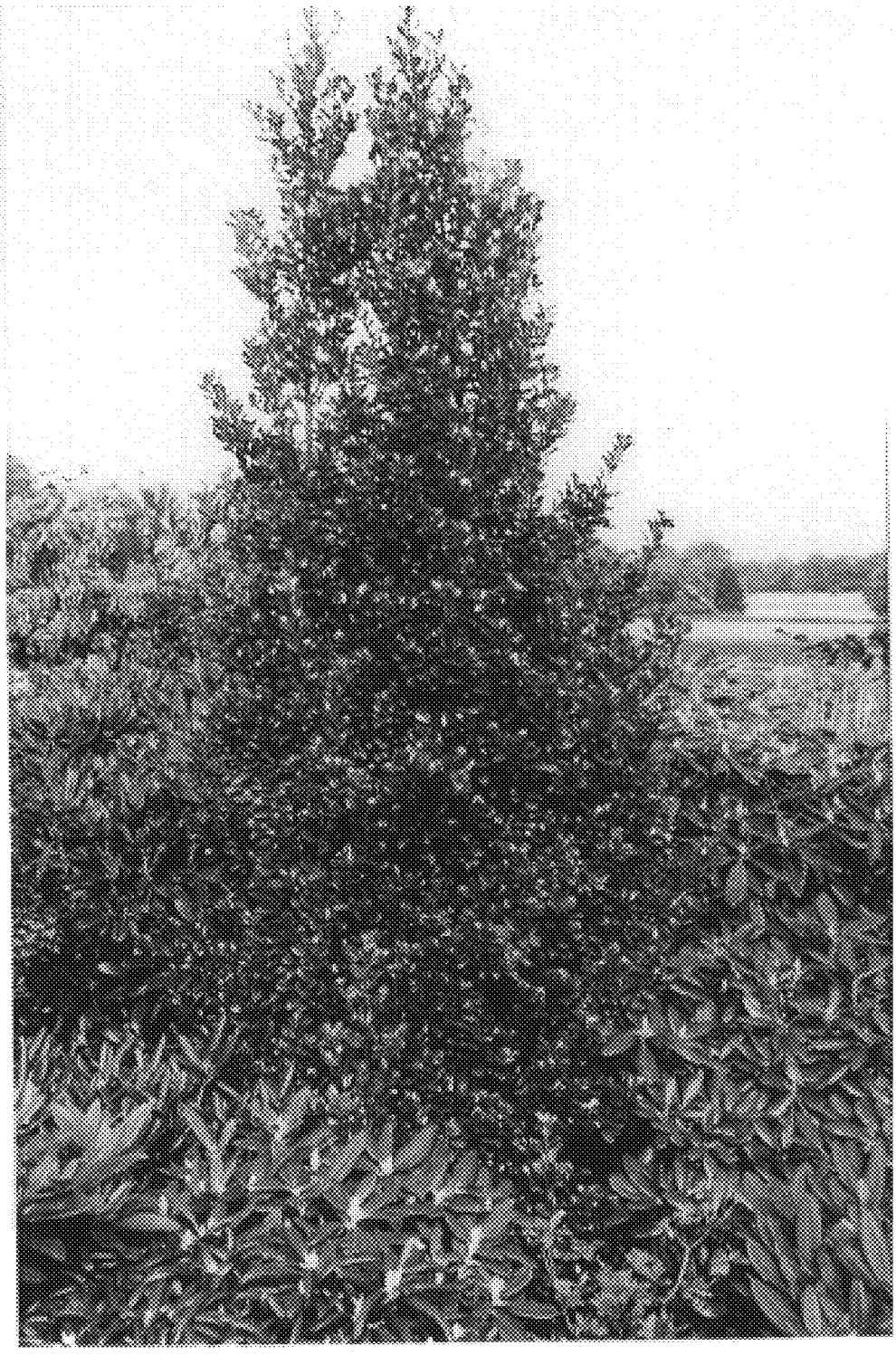
FIG. 2 shows the tree, 12 years old, about 250 cm tall.
Figure 3:
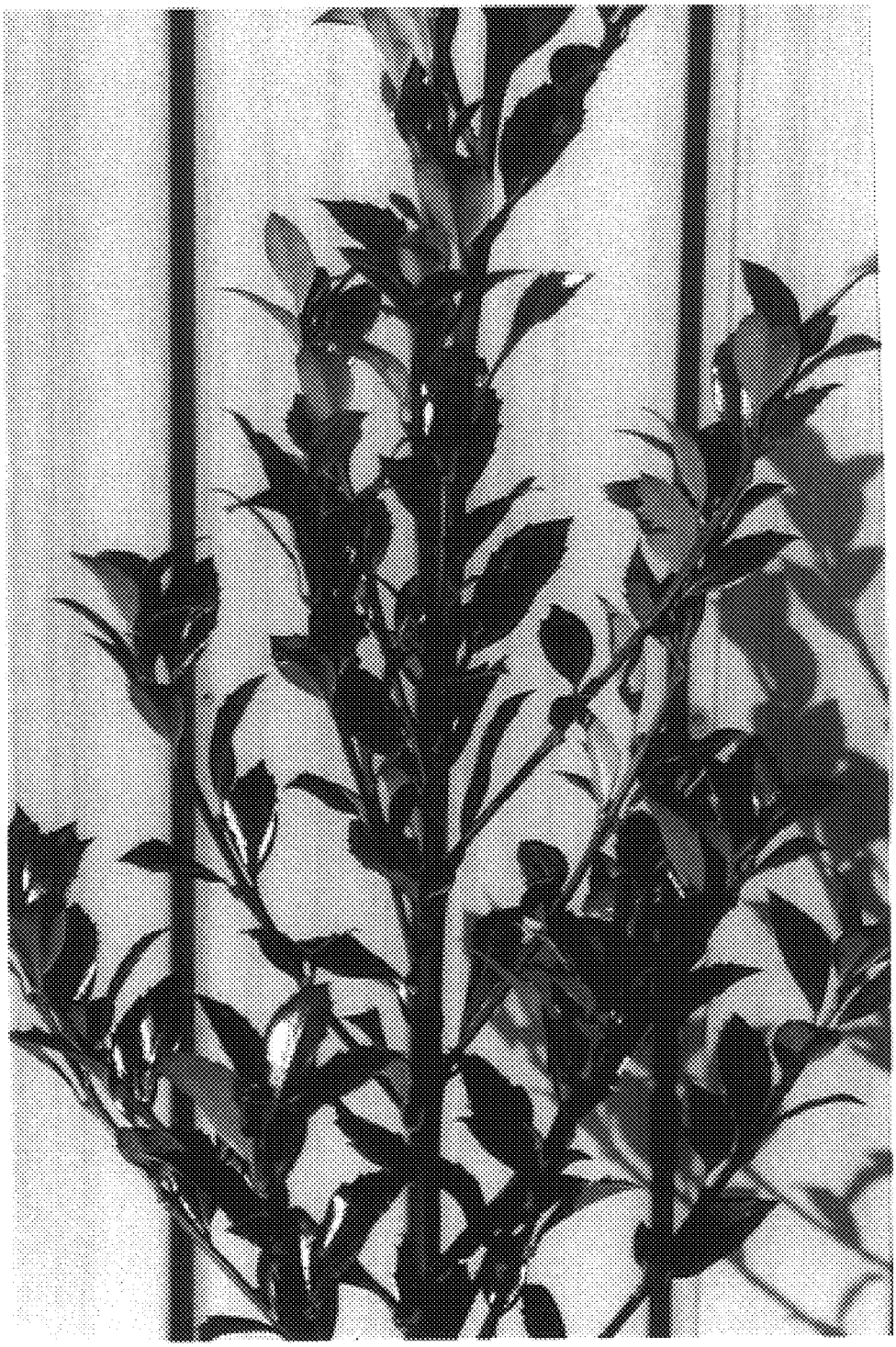
FIG. 3 shows the stem, branches, and leaves.
Figure 4:
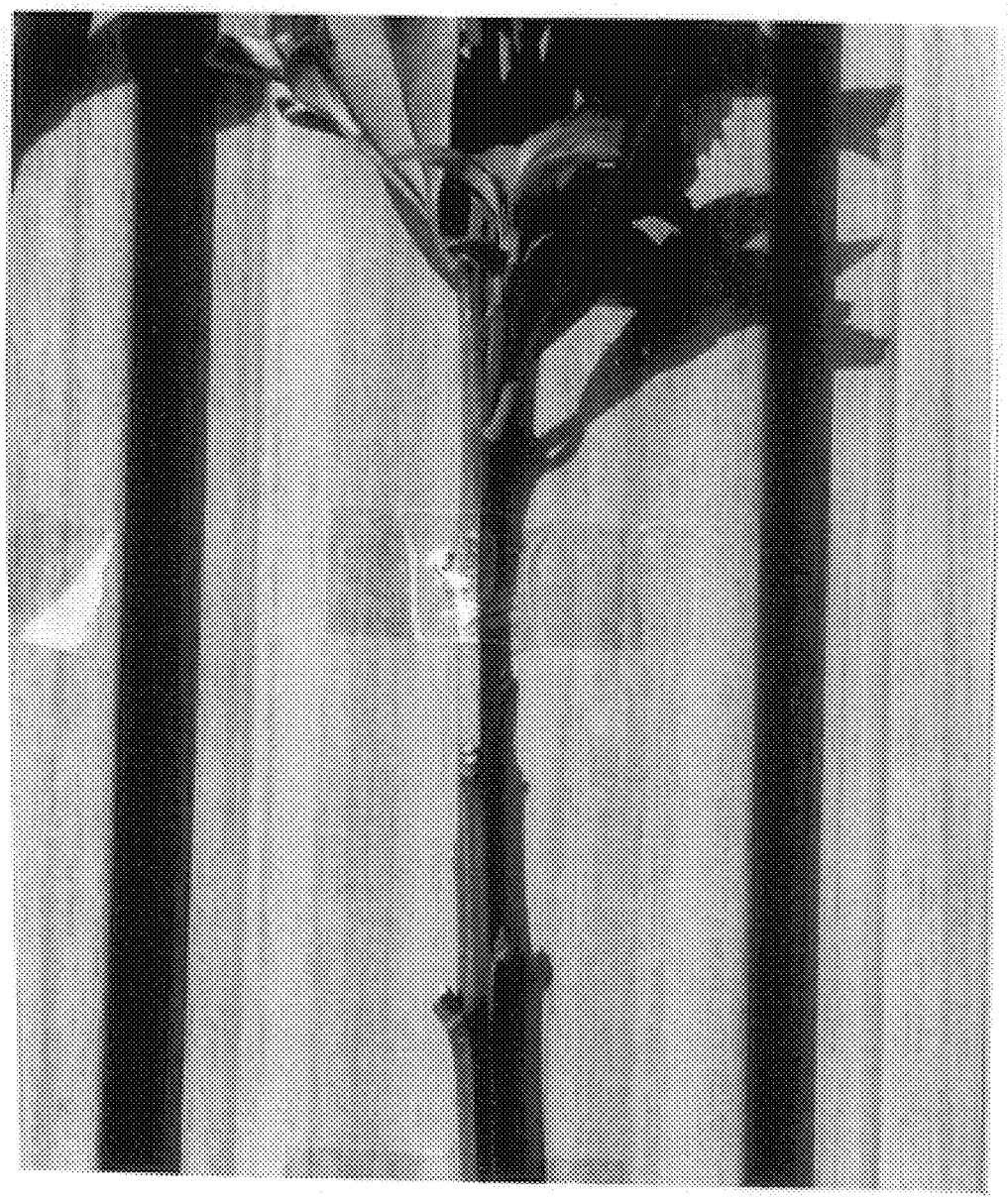
FIG. 4 shows a branch of a one-year old tree.
Figure 5:
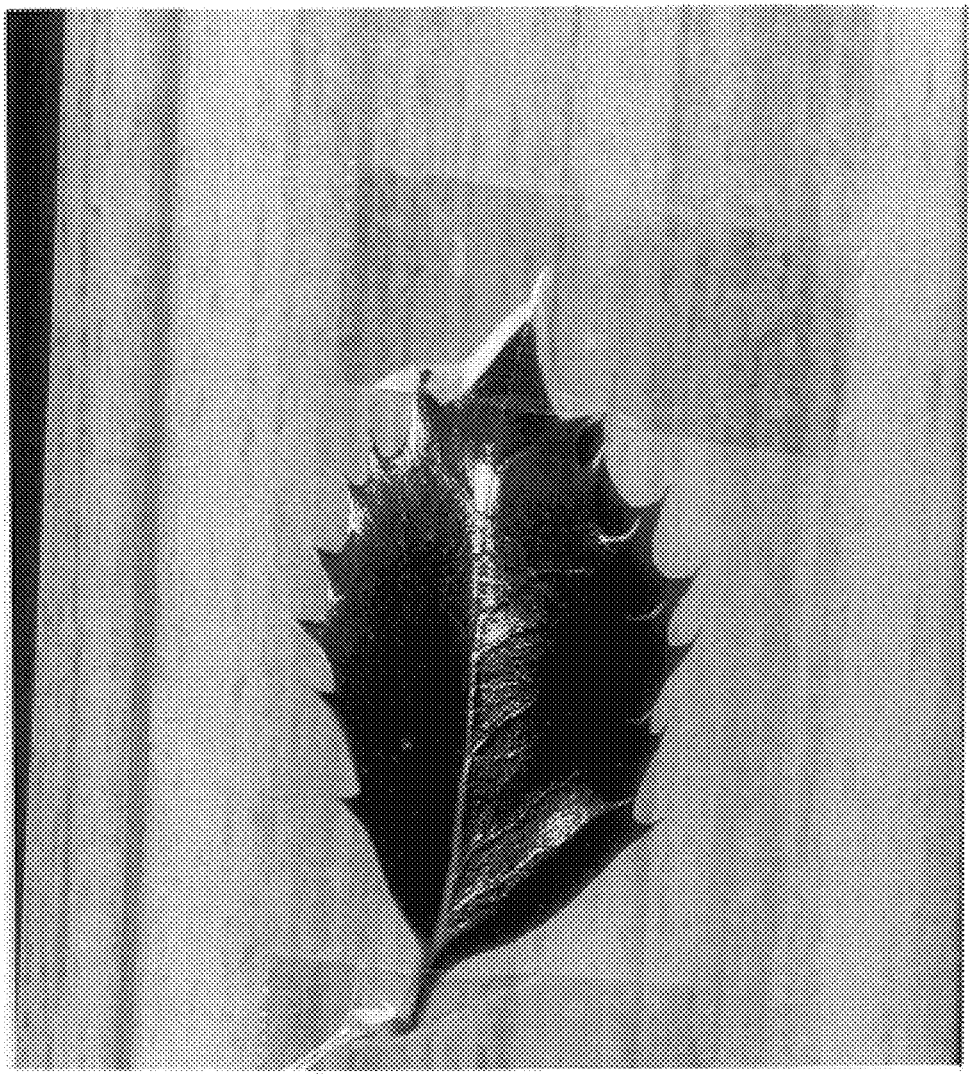
FIG. 5 shows the leaf upper surface.
Figure 6:
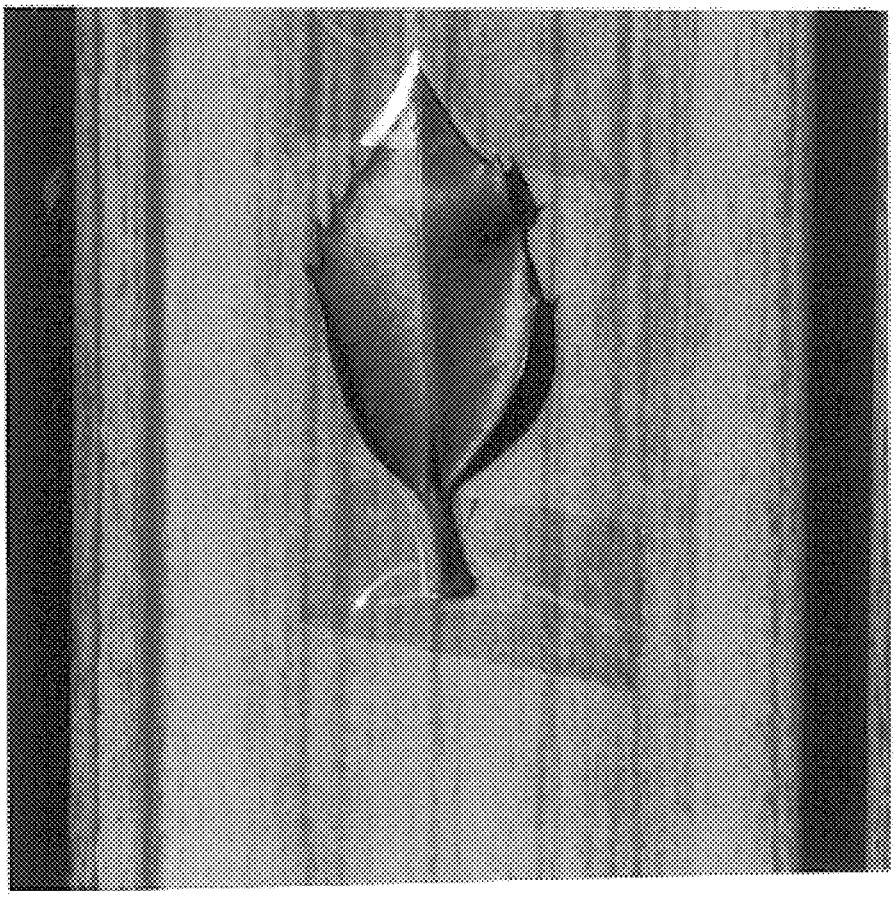
FIG. 6 shows the leaf lower surface.

The following detailed description sets forth the characteristics of the new cultivar. The data which defines these characteristics were collected from asexual reproductions carried out in Barmstedt, Germany. The plant history was taken on a plant about ten years old, grown from a 1.80 m rootball. The test plants were grown outdoors at about 8–10° C. nightime temperatures and color readings were taken outdoors.

In the following description, color references are made to The Royal Horticultural Society Colour Chart except where general terms of ordinary dictionary significance were used.

PLANT

Habit and form of growth: Upright, close habit.
Time to initiate root development: 3 months.
Plant vigor: Young plant grows 50–75 cm per year.
Plant height: 200 cm.
Plant width: 80 cm.
Average trunk diameter: 3.5 cm at 1 meter above soil level; measured at 15 years of age.
Average branch diameter: 5 mm.
Bark color: 79 A.

STEM AND LENTICEL

Young stem (1 year old):
*Color.*—79A.
*Texture.*—Rough.
Mature stem (2–5 years old):
*Color.*—146A with a hint of 137A.
*Texture.*—Rough.
Immature lenticel (1 year old):
*Shape.*—Elongated.
*Position relative to stem surface.*—Irregularly grouped.
*Average length.*—0.5–0.8 mm.
*Average width.*—0.2–0.5 mm.
*Quantity.*—3–8 per square inch.
*Color.*—145B.
Mature lenticel (2–3 years old):
*Shape.*—Nearly round.
*Position relative to stem surface.*—Irregularly grouped.
*Average length.*—1 mm.
*Average width.*—1 mm.
*Quantity.*—4–8.
*Color.*—152A.

FOLIAGE

Internode length: 30 mm.
Margin: Serrated.
Spine quality and location: 9–13 spines at the margin.
Size of mature leaves:
*Length.*—4 cm.
*Width.*—2.5 cm.
Shape of mature leaves: Oval, slightly curved.
Juvenile leaves:
*Upper surface.*—Texture: Smooth, slightly glossy. Color: 143B. Venation color: 144B.
*Lower surface.*—Texture: Rough. Color: 144A. Venation color: 144A.
Mature leaves:
*Upper surface.*—Texture: Smooth. Color: 139A. Venation color: 137C.
*Lower surface.*—Texture: Rough. Color: 144A. Venation color: 139B.
Petiole:
*Length.*—6–8 mm.
*Diameter.*—2 mm.
*Color.*—144A with hint of 137A.
Leaf arrangement: Helical around the twig.

FLOWERS

Habit: In clusters of 3 to 6 flowers.
Peduncle:
*Texture.*—Velvety, rough.
*Size.*—Length: 2–3 mm. Diameter: 3 mm.
*Color.*—157B.
Calyx:
*Diameter.*—6–8 mm when fully open.
*Texture.*—Velvety, rough.
Buds:
*Shape* (*prior to opening*).—Spherical; 4 mm circumference.
*Color, upon opening.*—157A.
*Color changes during opening.*—None.
*Foliaceous appendages, color.*—157C.
Blooms:
*Petals.*—Four, not imbricated.
*Texture.*—Upper surface: Rough. Lower surface: Rough.
*Petal size.*—Width: 6 mm. Length: 6 mm.
*Shape of bloom.*—Cupped.
*Petal color.*—Upper surface: 155A. Lower surface: 157D.
Fragrance: Lemony.
Persistence on plant: 5–7 days.
Sepals:
*Length.*—3 mm.
*Width.*—3 mm.
*Number.*—4.
*Color.*—157 D.

REPRODUCTIVE ORGANS

Stamens:
*Number.*—4.
*Anther.*—Shape: Oval. Length: 1 mm. Color: 1C.
*Filament.*—Length: 2 mm. Color: 156D.
*Pollen.*—Amount: 4 spores per flower. Color: 10C.
Pistils:
*Quantity.*—One.
*Stigma.*—Shape: Round. Color: 157B.
Ovaries:
*Quantity.*—One.
*Size.*—1–1.5 mm.
*Color.*—138D.
Disease/pest resistance: Appears to be very disease and insect resistant.
Winter hardiness: Extremely hardy to −25° C. in snowless winter in north Germany.
Drought/heat tolerance: Resists temperatures up to 40° C.

I claim:

1. A new and distinct holly plant substantially as shown and described.

* * * * *